(12) United States Patent
Colling

(10) Patent No.: US 10,265,037 B2
(45) Date of Patent: *Apr. 23, 2019

(54) X-RAY SHIELDING SYSTEM

(71) Applicant: GLOBAL IMAGING SOLUTIONS COMPANY, Livonia, MI (US)

(72) Inventor: Timothy P. Colling, Farmington Hills, MI (US)

(73) Assignee: GLOBAL IMAGING SOLUTIONS COMPANY, Livonia, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/851,276

(22) Filed: Dec. 21, 2017

(65) Prior Publication Data

US 2018/0220977 A1  Aug. 9, 2018

Related U.S. Application Data

(63) Continuation-in-part of application No. 15/834,782, filed on Dec. 7, 2017, which is a continuation-in-part of application No. 15/710,649, filed on Sep. 20, 2017, now Pat. No. 10,004,466, which is a continuation-in-part of application No. 15/617,509, filed on Jun. 8, 2017, now Pat. No. 9,877,688, which is a continuation-in-part of application No. 15/427,414, filed on Feb. 8, 2017, now Pat. No. 9,867,583.

(51) Int. Cl.
| | | |
|---|---|---|
| A61B 6/00 | (2006.01) |
| A61B 6/10 | (2006.01) |
| A47B 96/07 | (2006.01) |
| A47B 96/06 | (2006.01) |
| G21F 3/00 | (2006.01) |
| A61N 5/10 | (2006.01) |

(52) U.S. Cl.
CPC ............ *A61B 6/107* (2013.01); *A47B 96/067* (2013.01); *A47B 96/07* (2013.01); *G21F 3/00* (2013.01); *A61N 2005/1094* (2013.01)

(58) Field of Classification Search
CPC .......... A61B 6/104; A61B 6/0407; G21F 3/00
USPC ..................... 250/505.1, 515.1, 517.1, 519.1
See application file for complete search history.

(56) References Cited

U.S. PATENT DOCUMENTS

| | | |
|---|---|---|
| 5,099,135 A | 3/1992 | Gemmill |
| 5,417,225 A | 5/1995 | Rubenstein et al. |
| 5,981,964 A | 11/1999 | McAuley et al. |
| 6,448,571 B1 | 9/2002 | Goldstein |
| 6,653,648 B2 | 11/2003 | Goldstein |
| 6,703,632 B1 | 3/2004 | Macklis et al. |

(Continued)

FOREIGN PATENT DOCUMENTS

| | | |
|---|---|---|
| CN | 201127616 | 10/2008 |
| DE | 2614202 | 10/1977 |

*Primary Examiner* — Michael Maskell
(74) *Attorney, Agent, or Firm* — Brooks Kushman P.C.

(57) ABSTRACT

Disclosed is a shielding system for customized shielding of a patient or an operator from X-rays generated across a patient-supporting table. The shielding system includes a foundational block which is mounted via a clamping mechanism on the patient-supporting table. The shielding system has a rail with proximal and distal sections. The proximal section of the rail is twistable within an aperture of the foundational block and is arcuately movable in relation to patient-supporting table. One or more protective curtains are suspended from the rail.

17 Claims, 3 Drawing Sheets

(56) References Cited

U.S. PATENT DOCUMENTS

| | | |
|---|---|---|
| 9,177,681 B2 | 11/2015 | Morris |
| 9,451,922 B2 | 9/2016 | Buchmeyer |
| 9,867,583 B1 | 1/2018 | Colling |
| 9,877,688 B1 | 1/2018 | Colling |
| 10,004,466 B1 * | 6/2018 | Colling .................. A61B 6/107 |
| 2012/0148335 A1 | 6/2012 | Nourry et al. |

* cited by examiner

X-RAY SHIELDING SYSTEM

CROSS-REFERENCE TO RELATED APPLICATIONS

This application claims the benefit of and is a continuation-in-part of U.S. Ser. No. 15/834,782 filed Dec. 7, 2017, now U.S. Pat. No. 10,056,162 issued Aug. 21, 2018, which claims the benefit of and is a continuation-in-part of U.S. Ser. No. 15/710,649 filed Sep. 20, 2017, now U.S. Pat. No. 10,004,466 issued Jun. 26, 2018, which claims the benefit of and is a continuation-in-part of U.S. Ser. No. 15/617,509 filed Jun. 8, 2017, now U.S. Pat. No. 9,877,688 issued Jan. 30, 2018, which claims the benefit of and is a continuation-in-part of U.S. Ser. No. 15/427,414 which was filed on Feb. 8, 2017, now U.S. Pat. No. 9,867,583 issued Jan. 16, 2018, the disclosures of which are incorporated herein in their entirety.

TECHNICAL FIELD

This disclosure includes a customizable x-ray shielding system including a foundational block mounted on a patient-supporting table, the block supporting a bi-sectional rail with a transition region from which one or more radiopaque curtains may be suspended in an adjustable, desired orientation.

BACKGROUND

Among the art considered in preparing this patent application are these references: U.S. Pat. Nos. 5,099,135; 5,417,225; 6,448,571; and 6,653,648.

SUMMARY

Disclosed is a shielding system for customized protection from X-rays. The shielding system is mounted via a clamp on a table that supports a patient. The table, if desired, can be tilted so that it may lie in a plane that is about, for example, plus or minus 45 degrees from a horizontal plane.

In use over the various orientations of such tables there is a need to isolate the technician or physician from X-radiation. To do this, a radiation protection material or shielding device such as lead or other radio-opaque curtains are often used. But such curtains need to be suspended from a movable rail so that their placement is predictable, yet adjustable regardless of table orientation.

One way to achieve the goal of reliably supporting such shielding devices is to suspend them from a bi-sectional rail with a proximal section and a distal section. The proximal section is rotatably seated in a foundational block which is affixed via a clamping mechanism preferably to a longitudinal edge of a patient-supporting table. Extending from the proximal section is a transition region, and then the distal section, which in turn is preferably orthogonally disposed to the proximal section.

Optionally one or more lead curtains or their equivalents are suspended from the distal section. If desired, multiple foundational blocks may be affixed via clamping mechanisms to the table.

Details of a representative foundational block now follow. An operator-facing side of the foundational block generally extends upwardly from the table after the block is mounted to an edge thereof. Opposite that side is a patient-facing side. Across the top of the block is an upper face (B). One or more rail-receiving apertures extends at least partially between the upper face (B) and an opposing bottom face (A) which is positioned proximate to the table's generally horizontal surface. Each aperture is configured to receive a proximal end section of the rail. A radio-opaque curtain can be suspended from the arcuately movable rail under the influence of gravity in a vertical plane.

One or more detents are defined around a rail-receiving aperture by the upper face (B). At least some of the detents are configured to be in registration with one or more lugs that extend radially from the proximal end section of a rail. Upon registration, there is little or no twisting movement of the rail in relation to the foundational block.

In use, a rail can be turned within an associated aperture. Regardless of table orientation, one or more radio-opaque curtains can be suspended from the rail in a desired position by twisting the proximal end section, rotating it in relation to the associated aperture and then seating one or more lugs in a suitable detent.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
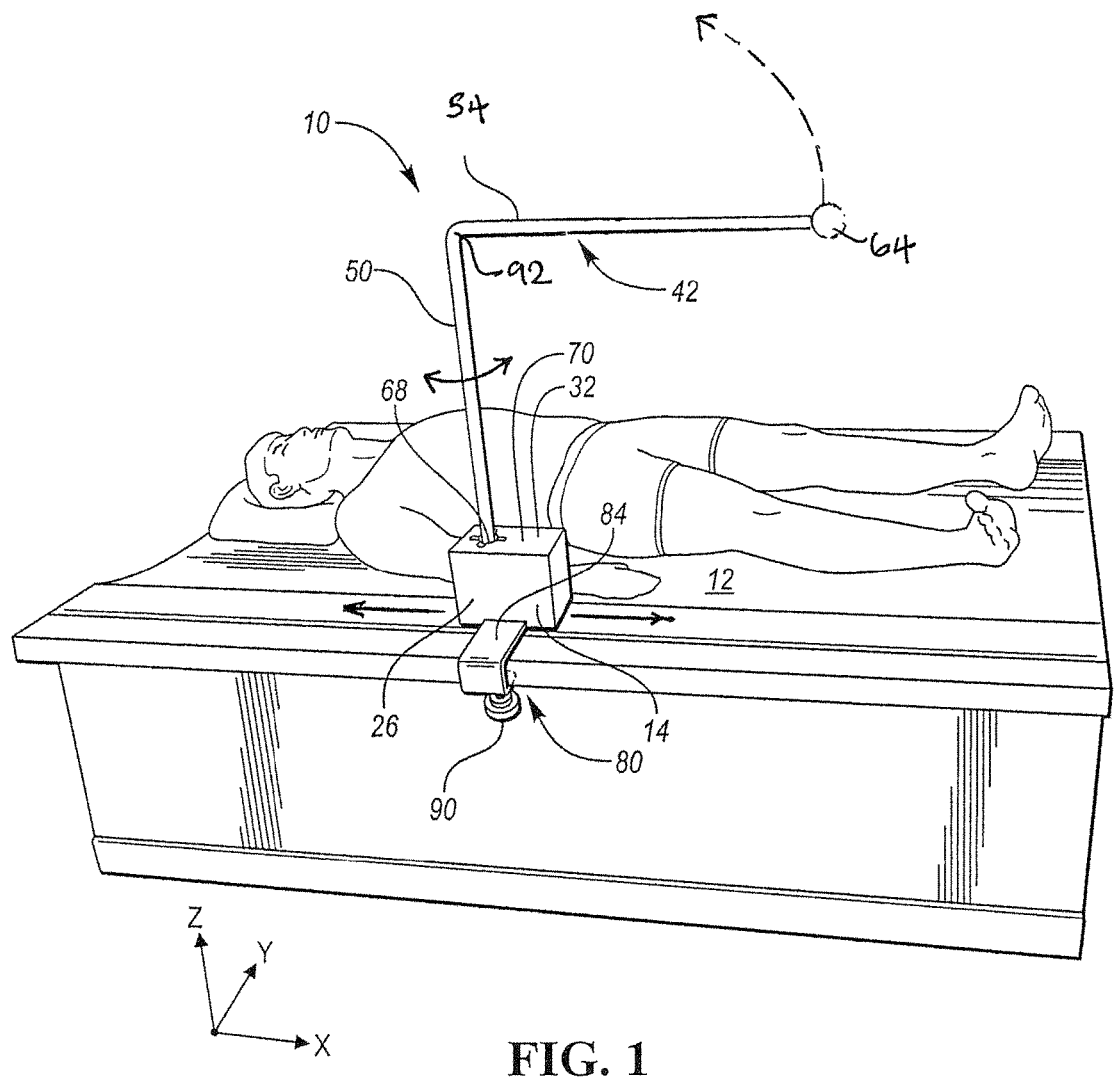
FIG. 1 is a quartering perspective view of a typical environment in which a shielding system is deployed, including a bi-sectional rail with a transition region between a proximal and distal section from which one or more lead curtains are to be suspended.

Disclosed is a shielding system 10 for use in alternative configurations as user-selected, customized shielding from X-rays. The shielding system 10 includes one or more foundational blocks 26 that are movably attached via a clamping mechanism to a patient-supporting table 12 (FIG. 1). In use, the usually near-horizontal plane of the patient-supporting table 12 can be tilted about a lateral axis if desired through an angular range of about 45 degrees from a horizontal plane.

Figure 2:
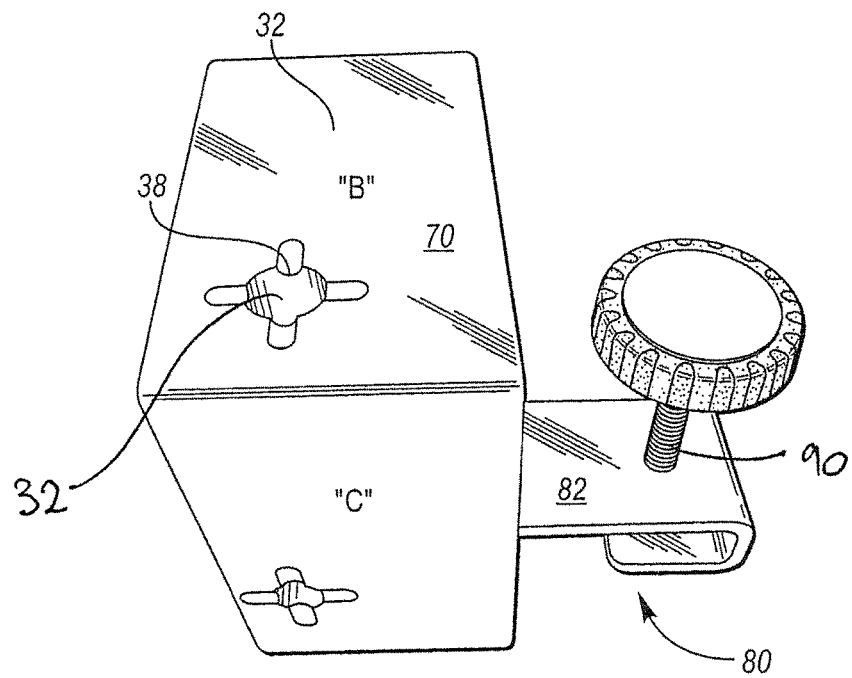
FIG. 2 is a quartering perspective view of a representative foundational block with a left side (C) and upper face (B) with detents around an aperture that receive lugs extending from a proximal end region of the rail.
Figure 3:
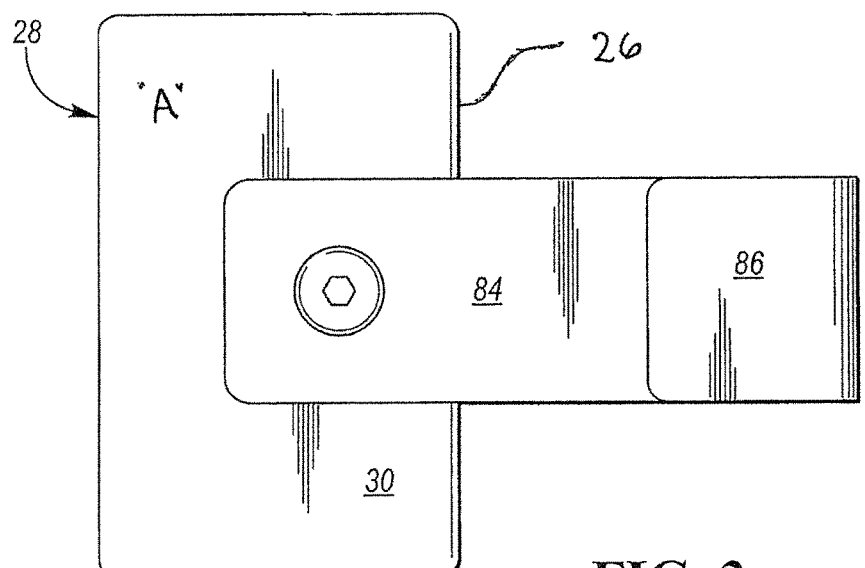
FIG. 3 is a view of a bottom face (A) of a representative foundational block with depicts a mounting bracket by which the block is mounted to a table.

Opposite an operator-facing side 14 is a patient-facing side 28 of a foundational block 26 (FIG. 3). One or more rail-receiving apertures 32 extend at least partially between the upper face (B) 70 (FIG. 2) and an opposing bottom face (A) 30 (FIG. 3). One or more detents 38 are defined within the upper face (B). Each major aperture is configured to receive a rail 42. Though four detents are shown, more or fewer detents 38 may be provided. Each detent 38 is configured to be in registration with one, two or more lugs or pins 68 that extend generally radially from a proximal section 50 of the rail 42. Upon registration of the rail 42 within an associated detent 38, there is little or no twisting movement of the rail 42 in relation to the foundational block 26. Preferably the apertures 32 terminate at the opposing faces 30, 70 (FIG. 2). The detents 38 extend radially from at least some of the apertures 32. The detents 38 are configured to engage lugs 68 that extend radially from the proximal section 50 of the rail 42 to preclude a twisting motion of the rail 42 when seated within an associated aperture 32. This feature influences rail positioning regardless of patient-supporting table orientation.

As a frame of reference, imagine (see, FIG. 1) that the longitudinal axis of the table 12 lies along an X-X axis and that across the table lies another axis Y-Y. Extending vertically from their intersection is an imaginary axis Z-Z.

Each rail 42 has a proximal section 50 (FIG. 1) lying parallel to the Y-Y axis that is received by a major aperture 32 of a foundational block 26. Extending from the proximal section 50 is a distal section 54 that lies parallel to the Y-Y axis or the X-X axis or is positioned therebetween. The proximal 50 and distal 54 sections are preferably orthogonally disposed. But not necessarily so. Other angular relationships between about 30 and 90 degrees may be desirable, depending on the installation.

Figure 4:
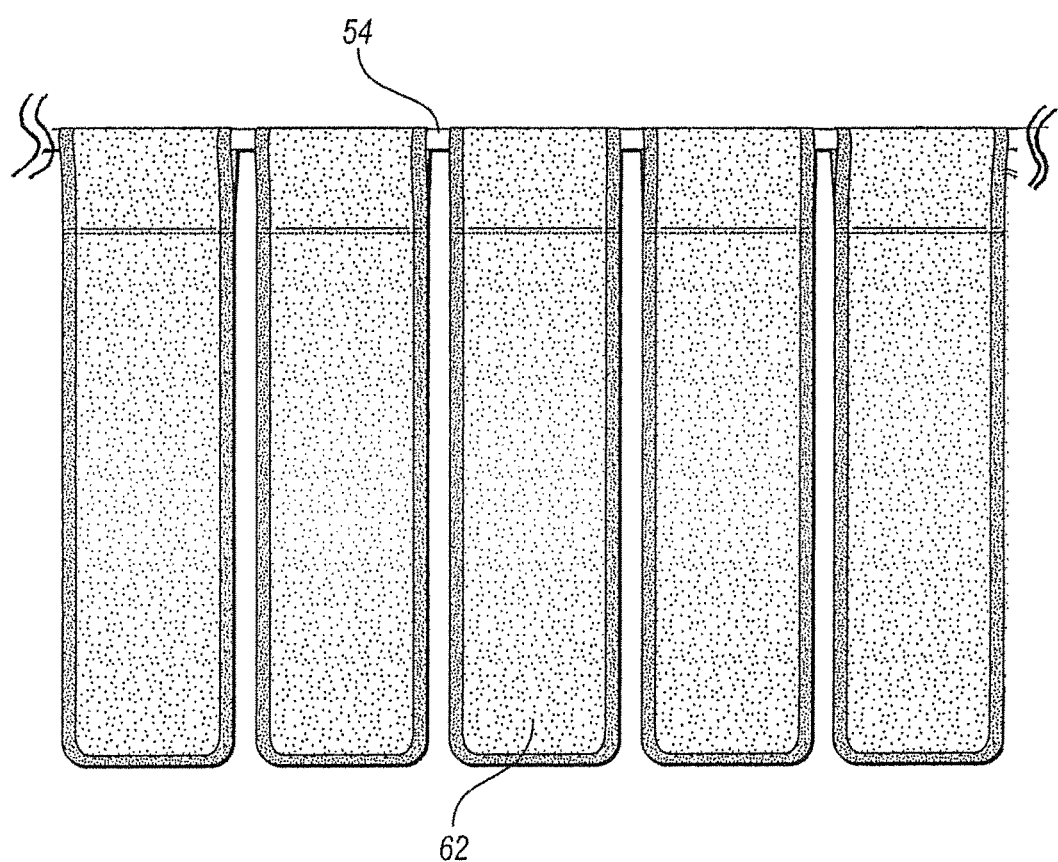
FIG. 4 illustrates one way in which to suspend radiation protection materials from a distal section of the rail.

Regardless of patient-supporting table orientation, one or more radio-opaque curtains 62 (FIG. 4) can be hung from the distal section 54 and/or an optional intermediate section (not shown) to allow flexibility in adapting to operator and patient examination requirements. It will be appreciated that the curtains 62 are preferably formed from an x-ray absorbing material. Such curtains 62 may for example be 20" long×26" wide. But the curtains 62 can be of any length and width. Further, the curtains 62 may have any desired x-ray attenuation characteristics.

In one embodiment, there is a knob 64 that is received at an end of the distal section 54 of the rail 42 for constraining lateral movement of the one or more radio-opaque curtains 62.

In most uses, the rail 42 can be twisted within an associated major aperture 32 so that the distal section 60 of the rail 42 can be made to extend substantially horizontally across or along the table regardless of patient-supporting table orientation.

In some cases, each patient-supporting table has one or two foundational blocks 26 for optimized shielding of the patient and operator from radiation. Each block 26 may support a rail 42. Preferably there are up to four blocks 26 per patient-supporting table. Placement of the block 26 is not restricted to a front face of the patient-supporting table. For example, a block could be secured if desired to a lateral side or back edge of the table.

To secure a foundational block 26 in relation to an edge of the patient-supporting table, a clamping mechanism or means for securement 80 are provided (FIG. 2). The securement means 80 include, for example, a U-shaped bracket 82 with two legs 84, 86, either or both of which defining a preferably threaded orifice. The bracket 82 is flush-mounted, for example, into the bottom face (A) (FIG. 3) and secured thereto by such affixing means as an Allen screw and the like. A threaded bolt 90 with a knurled head for example may be adjustably inserted into an orifice defined in one or the other leg of the U-shaped bracket 80. It will be appreciated that the securement means may also be embodied in a screw, a rivet, cement, a glue or a clamp.

In some cases, the patient-supporting table orientation lies between plus and minus 45 degrees from a horizontal plane.

Although the foundation blocks 26 are depicted as generally brick-shaped, it will be appreciated that such blocks may assume various geometries and sizes, and have non-parallel faces that may or may not be planar.

Positioned between the distal 54 and proximal 50 sections of the rail is a transition region 92. In some embodiments, the transition region 92 is effectively a joint that defines a right angle between the proximal and distal sections 50,54. In other embodiments, the transition region 92 may assume a curved configuration that extends therebetween. Thus, there is a more gradual transition between these two sections, in contrast to a fairly abrupt 90 degree change. In some further embodiments, the transition region may curve outside an Y-Z plane such that the distal section may not be co-planar with the proximal section, and be effectively offset therefrom.

| TABLE OF REFERENCE NUMERALS | |
|---|---|
| 10 | shielding system |
| 12 | table |
| 14 | front (operator-facing) side |
| 26 | foundational blocks |
| 28 | back (patient-facing) side |
| 30 | bottom face |
| 32 | rail-receiving aperture |
| 38 | detent |
| 42 | rail |
| 50 | proximal section of rail |
| 54 | distal section of rail |
| 62 | radiation protection material, e.g. radio-opaque curtain or lead apron |
| 64 | knob |
| 68 | lugs |
| 70 | upper face |
| 80 | means for securement |
| 82 | U-shaped bracket |
| 84, 86 | legs of 82 |
| 90 | threaded bolt |
| 92 | transition region |

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An x-ray shielding system for customized shielding from x-rays arising from treatment of a patient supported on a table with a longitudinal edge extending parallel to an imaginary (X-X) axis, the table having an imaginary lateral axis (Y-Y) extending there-across and an imaginary vertical axis (Z-Z) extending upwardly therefrom, the shielding system comprising:
   one or more foundational blocks detachably and slidably secured to the table, at least some blocks having:
      a bottom face and an opposing upper face;
      one or more rail-receiving apertures that extend at least partially between the bottom face and the opposing upper face; and
      a detent in the opposing upper face extending from an associated aperture, the detent being configured to be in registration with a lug that extends from a rail so that upon registration, there is little or no twisting of the rail in relation to the foundational block;

the rail being configured to support one or more radio-opaque curtains, the rail having:
a proximal section extending parallel to the (Z-Z) axis upwardly from the rail-receiving aperture; and
a distal section extending from the proximal section so that the radio-opaque curtains can be suspended from the distal section in an orientation that is suitable for the shielding needs of the patient and/or operator.

2. The shielding system of claim 1, further including:
a knob that is received at an end of the distal section of the rail for constraining lateral movement of the one or more radio-opaque curtains along the distal section of the rail.

3. The shielding system of claim 1, wherein one or more of the rail-receiving apertures terminate at the upper face and the detents extend radially from the one or more rail-receiving apertures, the detents being configured to engage lugs that extend radially from the proximal section of the rail to preclude a twisting motion of the rail within an associated aperture when the proximal section is seated in the rail-receiving aperture, thereby influencing rail positioning regardless of patient-supporting table orientation.

4. The shielding system of claim 1, wherein one rail orientation is such that the distal section is parallel to the (Y-Y) axis.

5. The shielding system of claim 1, wherein one rail orientation is such that the distal section is parallel to the (X-X) axis.

6. The shielding system of claim 1, wherein the rail can be twisted within the aperture when the lugs are disengaged from an associated aperture so that the distal section of the rail extends horizontally.

7. The shielding system of claim 1, wherein there are two foundational blocks, each supporting one or more rails, each rail having a distal section extending horizontally.

8. The shielding system of claim 1, further including means for securement associated with a foundational block that is adjacent an edge of the patient-supporting table to secure the foundational block in relation thereto.

9. The shielding system of claim 8, wherein the means for securement includes
a U-shaped bracket with two legs, one leg defining a threaded orifice, the bracket being associated with the bottom face.

10. The shielding system of claim 9, further including
a threaded bolt with a knurled head, the bolt being adjustably inserted into the orifice.

11. The shielding system of claim 1, wherein at least one of one or more foundational blocks has faces that are non-parallel and that may or may not be planar.

12. The shielding system of claim 1, wherein the distal section lies at an angle other than 90 degrees from the proximal section.

13. The shielding system of claim 1, wherein the distal section lies at an angle between about 30 and 90 degrees from the proximal section.

14. The shielding system of claim 1, wherein one foundational block has faces that are curved.

15. The shielding system of claim 1, further including a transition region between the proximal and distal sections, the transition region being a relatively abrupt transition or curved.

16. The shielding system of claim 15, wherein the transition region is shaped such that the distal section is not co-planar with the proximal section.

17. A method for customized shielding from x-rays arising from treatment of a patient supported on a table with a longitudinal edge extending parallel to an imaginary (X-X) axis, the table having an imaginary lateral axis (Y-Y) extending there-across and an imaginary vertical axis (Z-Z) extending upwardly therefrom, the method comprising the steps of providing:
one or more foundational blocks, each block having:
a bottom face and an opposing upper face;
one or more rail-receiving apertures that extend at least partially between the bottom face and the opposing upper face; and
a detent in the opposing upper face extending radially from an associated aperture, the detent being configured to be in registration with a lug that extends radially from a rail so that upon registration, there is little or no twisting of the rail in relation to the foundational block;
the rail being configured to support one or more radio-opaque curtains, the rail having
a proximal section extending parallel to the (Z-Z) axis upwardly from the rail-receiving aperture; and
a distal section extending from the proximal section so that the one or more radio-opaque curtains can be suspended therefrom; and
orienting the rail so that the curtain or curtains are positioned to suit the shielding needs of the patient and/or operator.

* * * * *